Figure 1:
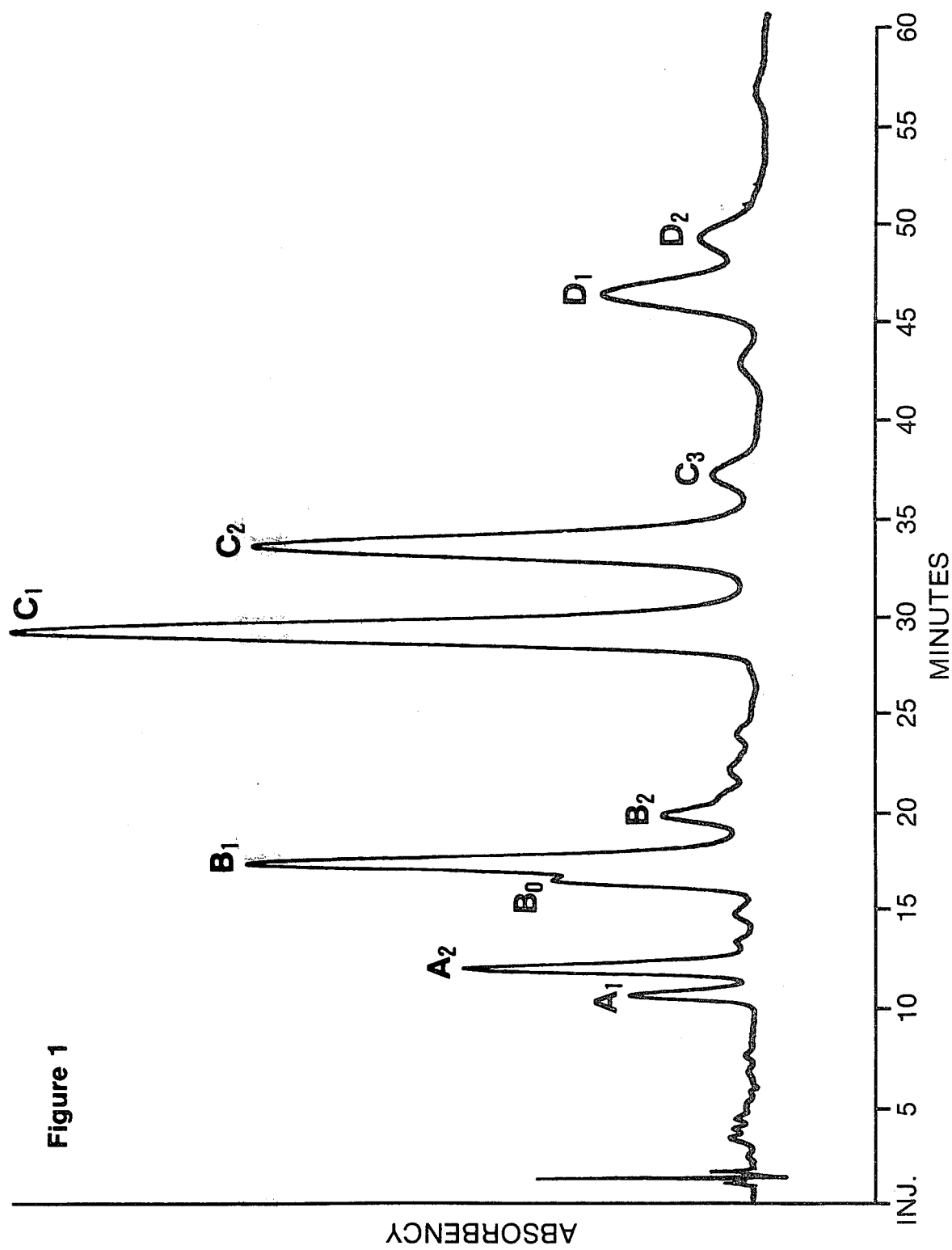

[19] United States Patent
Hamill et al.

[11] 4,336,333
[45] Jun. 22, 1982

[54] PROCESS FOR PREPARING TUNICAMYCIN

[75] Inventors: Robert L. Hamill, Greenwood; Marvin M. Hoehn; LaVerne D. Boeck, both of Indianapolis, all of Ind.

[73] Assignee: Eli Lilly and Company, Indianapolis, Ind.

[21] Appl. No.: 243,283

[22] Filed: Mar. 13, 1981

[51] Int. Cl.$^3$ .................. C12P 19/60; C12N 1/20; C12R 1/52
[52] U.S. Cl. ..................... 435/75; 435/253; 435/893
[58] Field of Search ................. 435/893, 75, 253

[56] References Cited

U.S. PATENT DOCUMENTS 3,960,667  6/1976  Gale et al. ............ 435/893
4,237,225  12/1980  Hamill ............ 435/75

OTHER PUBLICATIONS

A. Takatsuki et al., J. Antibiot. 24, 215-238 (1971).
K. Ekhardt et al., J. Antibiot. 28, 274-279 (1975).
A. Takatsuki et al., Agric. Biol. Chem. 41, 2307-2309 (1977).
A. Takatsuki et al., Agric. Biol. Chem. 43, 761 (1979).

Primary Examiner—Alvin E. Tanenholtz
Assistant Examiner—James Martinell
Attorney, Agent, or Firm—Dwight E. Morrison; Arthur R. Whale

[57] ABSTRACT

Tunicamycin is produced by the cultivation of *Streptomyces chartreusis* Calhoun and Johnson, 1956, NRRL 12338. Methods of recovering tunicamycin and for separating and isolating individual factors $A_1$, $A_2$, $B_1$, $B_2$, $C_1$, $C_2$, $D_1$ and $D_2$ from tunicamycin complex are described.

11 Claims, 1 Drawing Figure

PROCESS FOR PREPARING TUNICAMYCIN

Tunicamycin is a known antibiotic, and is described by A. Takatsuki et al., *J. Antibiot.* 24, 215–238 (1971). The antibiotic is produced by a strain of *Streptomyces lysosuperificus* (see Takatsuki, supra); by *Streptomyces LA*-507 (see Japanese Pat. No. 2079086); and by *Streptomyces chartreusis* NRRL 3882 [see U.S. Pat. No. 4,237,225 (Dec. 2, 1980)]. Minor antibiotic factors isolated from the streptovirudin complex produced by Streptomyces JA 10124 are reported to be related to tunicamycin [See K. Eckardt et al., *J. Antibiot.* 28, 274–279 (1975), and *Z. Allg. Mikrobiol.* 13, 625–627 (1973)].

Tunicamycin is a complex comprising a mixture of co-produced antibiotic factors. The four major factors of the tunicamycin complex have been shown by A. Takatsuki et al., *Agric. Biol. Chem.* 41, 2307–2309 (1977), to be antibiotics having the structural formula (I) depicted below:

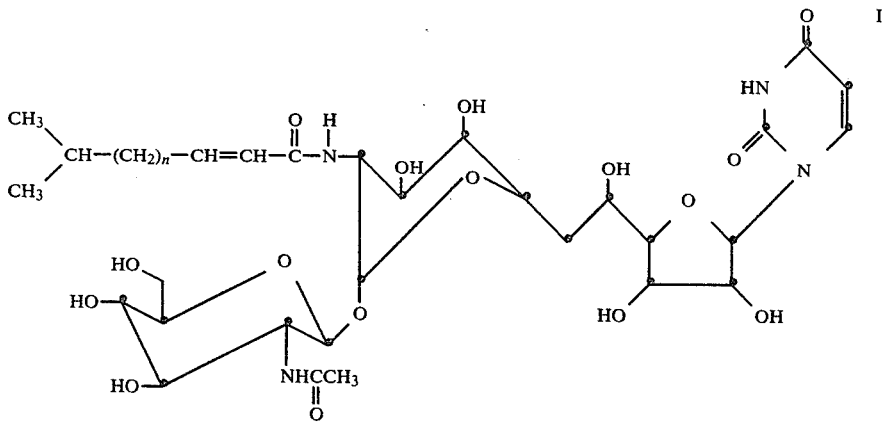

The individual factors are named, according to Takatsuki et al., as follows:

(1) Tunicamycin A, when n=9
(2) Tunicamycin B, when n=10
(3) Tunicamycin C, when n=8
(4) Tunicamycin D, when n=11

It is seen that tunicamycin A, B, C, and D differ only with respect to the chain length of the fatty acid residue substituted on the amino group of the tunicamine moiety. The structures of the individual factors were determined by Takatsuki from analysis of the degradation products formed after acid hydrolysis of tunicamycin.

The designation of the factors as reported by Takatsuki et al., supra, has been changed by us to conform to the elution pattern in chromatographic systems (HPLC and TLC), and increasing molecular weights. Thus, the factors of the tunicamycin complex are grouped according to molecular weight (isomers of the fatty acid moiety—e.g., $A_1$ and $A_2$; $B_1$ and $B_2$; $C_1$ and $C_2$; $D_1$ and $D_2$); minor factors with a molecular weight 2 daltons higher are also found for each series (e.g., 818 vs. 816, saturated fatty acid moieties rather than the unsaturated fatty acid moieties found in the major factors). Evidence for the different fatty acid moieties has been reported by Takatsuki et al., *Agric. Biol. Chem.*, 43, 761 (1979).

The correlation of the two designation systems, the configuration of the fatty acid moieties as determined by $^1$H-NMR, and the molecular weights as determined by field desorption mass spectrometry (FDMS), are shown in Table 1, which follows.

TABLE 1

| Takatsuki Designation | Our Designation | Mol. Wt.[1] (FDMS) | Type Fatty Acid[2] | n[3] |
|---|---|---|---|---|
| C | $A_1$ | 816 | I | 8 |
|  | $A_2$ | 816 | N | 8 |
| A | $B_1$ | 830 | I | 9 |
|  | $B_2$ | 830 | N | 9 |
| B | $C_1$ | 844 | I | 10 |
|  | $C_2$ | 844 | N | 10 |
| D | $D_1$ | 858 | N | 11 |
|  | $D_2$ | 858 | I | 11 |

[1]The molecule is cationized during the field desorption process and is observed at (N + Na), e.g., for A, at M/Z 839.
[2]I = isofatty acid [80.87 (doublet) indicated an isopropyl group]; N = normal fatty acid
[3]n = number of —$CH_2$— groups in Formula (I), supra.

The individual factors of each series are separated in pure form by preparative reverse-phase resin chromatography (HPLC). The pattern of elution and factor designation are shown in the analytical HPLC graph as

FIG. 1.

The separation of tunicamycin into the individual factors and the isolation thereof has been reported in U.S. Pat. No. 4,237,225 (Dec. 2, 1980).

As used herein and in the claims, "tunicamycin" means the complex comprising the co-produced major antibiotic factors known as tunicamycin $A_1$ and $A_2$, $B_1$ and $B_2$, $C_1$ and $C_2$, and $D_1$ and $D_2$. Additional minor factors are also present in the complex. It will be recognized by those skilled in the fermentation art that the number and ratio of individual factors produced in an antibiotic complex will vary depending on the fermentation conditions employed.

Tunicamycin has been reported to exhibit antibacterial and anti-viral activity in in vitro tests. [See Takatsuki et al., *Agric. Biol. Chem.* 41, 2307–2309 (1977)]. Tunicamycin is a potent inhibitor of glycoprotein synthesis, preventing the incorporation of sugar into protein cell wall constituents. The use of tunicamycin to study the mechanism of cell wall synthesis has been widely reported in the biochemical literature.

The present invention relates to novel methods of preparing the tunicamycin complex, and the tunicamycin isomers noted above. In particular, the invention constitutes a method of preparing tunicamycin which comprises cultivating *Streptomyces chartreusis* Calhoun and Johnson, 1956, NRRL 12338 in a culture medium containing assimilable sources of carbon, nitrogen, and inorganic salts under submerged aerobic conditions until a substantial amount of tunicamycin is produced, and recovering the tunicamycin. The invention also contemplates methods of preparing tunicamycin $A_1$ and $A_2$, tunicamycin $B_1$ and $B_2$, tunicamycin $C_1$ and $C_2$, and tunicamycin $D_1$ and $D_2$, which comprises preparing tunicamycin by cultivating *Streptomyces chartreusis* Calhoun and Johnson, 1956, NRRL 12338 according to the method described above; separating the desired factor from other co-produced factors; and recovering the desired factor. For the purpose of this invention, it is understood that each of the above-named individual factors is isolated in a form substantially free of other co-produced tunicamycin factors.

The new microorganism useful for producing the antibiotic tunicamycin was isolated from a soil sample collected in the Netherlands Antilles, and the culture was given the number A-44450 for internal identification purposes.

Culture A-44450 is classified as a strain of Streptomyces chartreusis Calhoun and Johnson, 1956, based upon a simultaneous culture of *Streptomyces chartreusis* ATCC 14922; *Streptomyces coerulescens* ATCC 19896; and *Streptomyces lanatus* ATCC 19775, using the methods and media recommended by Shirling and Gottlieb, "Methods of Characterization of Streptomyces Species", *Int. Bull. of Systematic Bacteriol.* 16, 313–340 (1966), along with certain supplementary tests, as well as by comparison with published descriptions. See R. E. Buchanan and N. E. Gibbons (eds.), Bergey's Manual of Determinative Bacteriology, page 658 (8th edition, 1974. The Williams and Wilkins Company, Baltimore); K. M. Calhoun and L. E. Johnson, "Taxonomic and Microbiologic Studies of *Streptomyces chartreusis* n.sp.", *Antibiot. Chemother.* 6(4), 294–298 (1956); T. G. Pridham, C. W. Hesseltine, and R. G. Benedict, "A Guide for the Classification of Streptomycetes According to Selected Groups", *Appl. Microbiol.* 6, 52–79 (1957); Shirling and Gottlieb, "Cooperative Description of Type Strains of Streptomyces", *Int. J. Syst. Bacteriol.* 8, 95, 96 (1968). From the characteristics observed, *Streptomyces chartreusis* ATCC 14922 was selected as being the most closely related species. The principle differences between the A-44450 culture and the above-noted Streptomyces cultures are in the production of antibiotic, the melanin production on ISP No. 7, nitrate reduction, salicin utilization, and starch hydrolysis.

Color names were assigned according to the ISCC-NBS method [ISCC-NBS Centroid color charts standard sample No. 2106, U.S. Department of Commerce, National Bureau of Standards (1958), Washington, D.C.]; and Color Harmony Manual, Fourth Edition, (Color Standards Department, Container Corporation of America, Illinois, 1958). Figures in parentheses refer to the Tresner and Backus color series [H. D. Tresner and E. J. Backus, "System of Color Wheels for Streptomycete Taxomony", *Appl. Microbiol.* 11, 335–338 (1956)]. The cell-wall sugars were determined using a modification of the procedure of M. P. Lechavalier, "Chemical Methods as Criteria for the Separation of Actinomyces into Genera". These methods were developed at workshops sponsored by the Subcommittee on Actinomyces of the American Society for Microbiology (Dr. Thomas G. Pridham, Convenor), and held at the Institute of Microbiology, Rutgers University, The State University of New Jersey, New Brunswick, N.J. (1971). The isomers of diaminopimelic acid were determined using the method of Becker et al., Appl. Microbiol. 11, 421–423 (1964).

CHARACTERIZATION OF TUNICAMYCIN-PRODUCING STRAIN

Morphology

Culture A-44450 produces well-developed aerial mycelia composed of sporophores coiled into spirals which are generally long, extended, open, and dextrorse, having three to seven coils. Some closed and tight spirals were also observed. This morphology is observed on all media which support aerial mycelia formation. The sporophores bear chains containing 10–50 oblong spores with spiny ornamentation.

Spores range in size from 0.52 to 0.84 microns in width and 0.75 to 1.29 microns in length, with average size about $0.64 \times 1.13$ microns. Hyphae measure 0.58 microns in diameter, and no coremia or sclerotia were seen.

TABLE 2

Cultural Characteristics of Culture A44450 and *S. chartreusis* ATCC 14922 on Various Media

|   |   | A44450 | *S. chartreusis* ATCC 14922 |
|---|---|---|---|
| ISP No. 2 | G: | abundant | abundant |
|   | R: | 71.m.OY | 71.m.OY |
|   | Am: | abundant (B) 19dc | abundant (B) 19fe |
|   | Sp: | none | none |
| ISP No. 3 | G: | abundant | abundant |
|   | R: | 90.gy.Y | 90.gy.Y |
|   | Am: | abundant (B) 19fe | abundant (B) 19fe to (GY)g |
|   | Sp: | none | none |
| ISP No. 4 | G: | abundant | abundant |
|   | R: | 94.1.01Br | 87.m.Y |
|   | Am: | abundant (B) 19dc | abundant (B) 19fe to (GY)g |
|   | Sp: | none | none |
| ISP No. 5 | G: | abundant | abundant |
|   | R: | 84.s.Y | 90.gy.Y |
|   | Am: | abundant (B) 19dc | abundant (B) 19fe to (GY)g |
|   | Sp: | none | none |
| ISP No. 7 | G: | abundant | abundant |
|   | R: | 78.d.yBr | 72.d.OY |
|   | Am: | abundant (B) 19dc | abundant (B) 19fe |
|   | Sp: | dark brown | none |
| Czapek's solution | G: | abundant | abundant |
|   | R: | 72.d.OY | 89.p.Y |
|   | Am: | trace (W)b | abundant (W)b |
|   | Sp: | none | none |

G = growth
R = reverse
Am = aerial mycelia
Sp = soluble pigment

Carbon utilization was determined using ISP No. 9 basal medium to which filter-sterilized carbon sources were added to equal a final concentration of 1.0 percent. The plates were incubated at 30° C. and read after 14 days.

The results of the carbon utilization test carried out with culture A-44450 and *S. chartreusis* ATCC 14922 are set forth in Table 3.

TABLE 3

Utilization of Carbon Compounds by Culture A44450 and *S. chartreusis* ATCC 14922

| Carbon Source | A44450 | *S. chartreusis* ATCC 14922 |
|---|---|---|
| no carbon source | − | − |
| D-Glucose | + | + |
| L-Arabinose | + | + |
| Sucrose | + | + |
| D-Xylose | + | + |
| i-Inositol | + | + |
| D-Mannitol | + | + |

TABLE 3-continued

Utilization of Carbon Compounds by
Culture A44450 and *S. chartreusis* ATCC 14922

| Carbon Source | A44450 | S. chartreusis ATCC 14922 |
| --- | --- | --- |
| D-Fructose | + | + |
| L-Rhamnose | + | + |
| Raffinose | + | + |
| Salicin | ± | + |
| D-Galactose | + | + |
| Cellobiose | + | + |
| D-Maltose | + | + |
| Glycerol | + | + |
| D-Arabinose | + | ND |
| Melibiose | + | ND |
| D-Ribose | + | ND |
| Tween 20 | + | ND |
| Tween 40 | + | ND |
| Tween 60 | + | ND |
| Tween 80 | + | ND |
| Tween 85 | + | ND |

ND = not done
+ = carbon utilized
− = carbon not utilized

CELL WALL STUDIES

Using hydrolyzed whole cells of the organism, the presence of certain diagnostic sugars was determined. Isolated cell walls were used to determine the isomers of diaminopimelic acid. The results of these studies are set forth above.

| Test | Result Observed |
| --- | --- |
| Isomers of diaminopimelic acid | LL-isomer |
| Diagnostic sugars detected | Glucose, Ribose |

Melanoid pigment production (chromogenicity) was determined with ISP No. 1 (tryptone-yeast extract broth), ISP No. 6 (peptone-yeast extract iron agar), ISP No. 7 (tyrosine agar), and modified ISP No. 7, which has the tyrosine removed.

Starch hydrolysis was determined by testing for the presence of starch with iodine on ISP No. 4 (inorganic salts-starch agar) plates following the methods of Blazevic and Ederer, "Principles of Biochemical Tests in Diagnostic Microbiology" [136 pp., John Wiley and Sons, New York (1975)].

Casein, esculin, hypoxanthine, tyrosine, xanthine decomposition, and lysozyme resistance, were all determined as described by Berd, "Laboratory Identification of Clinically Important Aerobic Actinomycetes", *Appl. Microbiol.* 25, 665–681 (1973).

Sodium chloride and sucrose tolerance were measured by adding each to ISP No. 2 agar to equal the concentrations desired.

The pH range for growth was measured using the following buffers at 0.05 M in yeast-malt extract agar plates (ISP No. 2): citric acid, pH 3, 4, 5; 2-[N-morpholino]ethane sulfonic acid (MES), pH 6 (Sigma Chemical Co.); 3-[N-morpholino]propane sulfonic acid (MOPS), pH 7 (Aldrich Chemical Co.); N-[tris(hydroxymethyl)methyl]glycine (Tricine), pH 8 (CalbioChem); 2-(cyclohexylamino)ethane sulfonic acid (CHES), pH 8.5, 9.0, 9.5 (P-L Biochemicals, Inc); 3-cyclohexylamino-1,1-propane sulfonic acid (CAPS), pH 10.0, 10.5 (P-L Biochemicals, Inc). The pH values of the agar plates were measured with a flat surface electrode prior to inoculation.

The methods of Blazevic and Ederer, supra, were followed for the catalase, phosphatase, and urease assays.

The characteristics determined by the aboveoutlined tests are reported in Table 4, which follows.

TABLE 4

Additional Characteristics

| | A44450 | S. chartreusis ATCC 14922 |
| --- | --- | --- |
| Casein decomposition | + | ND |
| Catalase | + | ND |
| D'Nase production | + | ND |
| Esculin decomposition | + | ND |
| Gelatin liquefaction | ± | + (slow) |
| Hypoxanthine decomposition | + | ND |
| Lysozyme resistance | − | ND |
| Melanoid pigments | + | + |
| Morphology | S | S |
| NaCl tolerance % | 6 | 7 |
| Nitrate reduction | − | + |
| pH range | 6.1–9.2 | ND |
| Phosphatase | + | ND |
| Skim milk | − | + |
| Spore shape | oblong | oblong |
| Spore size | 0.64 × 1.13 μM | *0.38 × 0.73 μM |
| Spore surface | spiny | spiny |
| Starch hydrolysis | − | + |
| Streptomycin sensitivity | + | + |
| Sucrose tolerance % | 40 | ND |
| Temperature range °C. | 15–40 | ND |
| Tyrosine decomposition | + | ND |
| Urease production | + | ND |
| Xanthine decomposition | + | ND |

ND = not done
* = measurements calculated from a photograph from Shirling and Gottlieb, supra.

Antibiotic sensitivity was determined with sensitivity discs padded onto the surface of seeded agar plates. ISP No. 2 agar plates seeded with 2% inoculum were used. The results are recorded in Table 5, which follows.

TABLE 5

Antibiotic Sensitivity of Culture A44450

| Conc. | Antibiotic | Type Compound | A44450 |
| --- | --- | --- | --- |
| 30 mcg. | Cephalothin | β-lactam | − |
| 30 mcg. | Chloromycetin | chloromycetin | + |
| 15 mcg. | Erythromycin | macrolide | + |
| 30 mcg. | Novobiocin | novobiocin | + |
| 10 units | Penicillin G | β-lactam | − |
| 5 mcg. | Rifampin | ansamycin | + |
| 10 mcg. | Streptomycin | aminoglycoside | + |
| 30 mcg. | Tetracycline | tetracycline | + |
| 30 mcg. | Vancomycin | glycopeptide | + |

Results:
+ = sensitive, zones of inhibition
− = resistant, no zones of inhibition The tunicamycin-producing *Streptomyces chartreusis* Calhoun and Johnson, 1956, organism has been deposited and made a part of the stock culture collection of the Northern Regional Research Center, U.S. Department of Agriculture, Agricultural Research Service, Peoria, Illinois, 61604, from which it is available to the public under the accession number NRRL 12338.

As is the case with other organisms, the characteristics of the tunicamycin-producing culture, *Streptomyces chartreusis* Calhoun and Johnson, 1956, NRRL 12338, are subject to variation. For example, artificial variants and mutants of the NRRL 12338 strain may be obtained by treatment with various known mutagens, such as ultraviolet rays, X-rays, high frequency sound waves, radioactive rays, and chemicals. All natural and artificial variants and mutants of *Streptomyces chartreusis* Calhoun and Johnson, 1956, NRRL 12338, which produce tunicamycin, may be used in this invention.

A number of different media may be used to produce tunicamycin with *Streptomyces chartreusis* Calhoun and Johnson, 1956, NRRL 12338. These media should contain assimilable sources of carbon, nitrogen, and inorganic salts. Suitable carbon sources include glucose, starch, and dextrin. Suitable nitrogen sources include peptone, enzyme-hydrolyzed casein, cottonseed meal, and meat peptone.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of tunicamycin employing NRRL 12338, submerged aerobic fermentation in tanks is utilized. However, small amounts of tunicamycin may be obtained by shake-flask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively-growing culture of the organism. The vegetative inoculum is then transferred to a larger tank where, after a suitable incubation time, the tunicamycin antibiotic is produced in optimal yield.

This tunicamycin-producing organism can be grown over a broad temperature range of from about 25 to about 37° C. Optimum production of tunicamycin with NRRL 12338 appears to occur at a temperature of about 30°–34° C.

As is customary in aerobic submerged culture processes, sterile air is dispersed through the culture medium. For efficient growth of the organism, the volume of air used in tank production is in the range of from about 0.25 to about 1.0 volume of air per volume of culture medium per minute (v/v/m), preferably about 0.25 v/v/m. An optimum rate in a 100-liter vessel is about 0.25 v/v/m with agitation provided by conventional impellers rotating at about 200–250 RPM.

It may be necessary to add small amounts (i.e., 0.2 ml./L.) of an antifoam agent such as propyleneglycol to large-scale fermentation media if foaming becomes a problem.

Production of the tunicamycin antibiotic can be monitored during the fermentation by either agar diffusion or turbidimetric methods. Test organisms suitable for use include *Saccharomyces pastorianus* and *Bacillus subtilis* ATCC 6633.

Antibiotic activity is generally present after about 40 hours and remains present for at least 4 or more days during the fermentation period. Peak antibiotic production occurs from about 4 to about 6 days fermentation time.

The tunicamycin antibiotic can be recovered from the fermentation medium by methods known in the art and described by Hamill in U.S. Pat. No. 4,237,225.

After completion of the fermentation using *Streptomyces chartreusis* Calhoun and Johnson, 1956, NRRL 12338, tunicamycin is present both in the mycelia and in the broth. Most of the tunicamycin is present, however, in the mycelia. The mycelia are collected by conventional means, such as by filtration (using a filter aid, if desired) or by centrifugation. Tunicamycin can be recovered from the mycelial filter cake and from the filtered broth by methods well known in fermentation technology, such as solvent extraction, precipitation, and chromatography.

Tunicamycin present in the mycelial filter cake can be removed therefrom by washing the cake with a water-miscible lower alkanol (e.g. methanol, ethanol, or propanol). Tunicamycin present in the aqueous mycelial alkanol extracts (obtained after evaporation of the alkanol) or in the filtration broth (obtained by removal of mycelia) can be recovered by extraction with a water-immiscible lower alkanol (e.g. n-butanol or n-amyl alcohol) or by chromatography using various adsorbents. Among suitable adsorbents are carbon, Diaion HP-20, Amberlite XAD-2, Amberlite XAD-4, or Amberlite X-384. Purification of crude tunicamycin (obtained after extraction into a water-immiscible alkanol or after chromatography) can be achieved by precipitation (e.g., from methanol to which is added acetone) or by re-chromatography. Suitable chromatographic adsorbents are those named above and, in addition, silica gel, alumina, Florisil, Sephadex G-15, Sephadex G-25, Sephadex LH-20, and reverse phase resins such as silica gel/$C_8$ or silica gel/$C_{18}$. Diaion resin is available from Mitsubishi Chemical Industries, Tokyo; the Amberlite resins are available from Rohm annd Haas Co., Philadelphia, Pa.; the Sephadex resins are available from Pharmacia Fine Chemicals AB, Uppsala, Sweden; Florisil is available from Floridin Co., Tallahassee, Fla.; and LiChroprep RP 8 (silica gel/$C_8$) and Lichroprep RP 18 (silica gel $C_{18}$) are available from E. Merck, Darmstadt, Germany. The preparation of a high loading capacity silica gel/$C_{18}$ from silica gel type LP-1 (10–20 microns, Whatman) is described in Example 6.

Silica gel and Diaion HP-20 are preferred adsorbents for the initial purification of tunicamycin. With silica gel, the impure tunicamycin, dissolved in methanol-water (1:1), is mixed with sufficient silica gel to adsorb all the liquid. A slurry of the moist adsorbent is added to a silica gel column packed in acetonitrile-water (9:1). The collected fractions are monitored by bioassay using *Bacillus subtilis* ATCC 6633 as the detecting organism. With Diaion HP-20, the impure tunicamycin, in water solution (which can be the filtered broth after removal of mycelia or aqueous solutions obtained after the alcohol extraction of the mycelia) is placed on a column packed in water. After washing with water, the column is eluted with methanol-water (1:1), which removes impurities, and with methanol, which removes tunicamycin.

Reverse phase high pressure liquid chromatography using silica gel/$C_{18}$ adsorbent is a preferred method for the final purification of tunicamycin. In this method, tunicamycin (as obtained, for example, after chromatography using silica gel or Diaion HP-20), dissolved in water or methanol-water (2:1), is placed on a column equilibrated with methanol-water (2:1) at a pressure of 60–85 psi. The column is then eluted at the above pressure with methanol-water (2:1) to remove further impurities and with methanol-water (4:1) to remove tunicamycin. The fractions, as they are eluted, are monitored with an ultraviolet spectrometer at 254 nm.

When it is desired to obtain the individual factors (tunicamycin $A_1$, $A_2$, $B_1$, $B_2$, $C_1$, $C_2$, $D_1$, or $D_2$), tunicamycin can be separated by chromatographic techniques, such as reverse-phase high performance liquid chromatography.

The tunicamycin complex can be analyzed using silica gel/$C_{18}$ HPLC analytical columns. Thus, a 10 microgram sample of tunicamycin [10 microliters of a solution of 1 mg./ml. of tunicamycin in methanol:water (7:3)] is applied to a Zorbax ODS column measuring 4 mm.×25 cm. [E. I. duPont de Nemours & Co., Inc., Wilmington, Del.]. The separation is accomplished at a flow rate of 2 ml./min., using an LDC Consta Metric III Pump and a Spectromonitor III Model 1204 linked with a Chromatograph Control Module (Laboratory Data Control, Division of Milton Roy Co., Riviera Beach, Florida), and a Printer/Plotter TISPP6000 (Houston Instrument, Division of Bausch & Lomb, Austin, Texas). Monitoring is accomplished by measuring ultraviolet absorption at 254 nm. The Retention Times and Percent Concentration of the several identified factors of tunicamycin are listed in Table 6, which follows.

TABLE 6

| Factor | Retention Time (Minutes) | Percent Concentration |
| --- | --- | --- |
| $A_1$ | 10.65 | 2.3 |
| $A_2$ | 12.05 | 5.8 |
| $B_0$ | 16.55 | 3.8 |
| $B_1$ | 17.40 | 16.0 |
| $B_2$ | 19.85 | 2.2 |
| $C_1$ | 29.05 | 29.9 |
| $C_2$ | 33.35 | 23.5 |
| $C_3$ | 37.00 | 1.4 |
| $D_0$ | 42.65 | 1.1 |
| $D_1$ | 46.15 | 9.2 |
| $D_2$ | 48.95 | 4.0 |

This HPLC separation of the tunicamycin factors can also be described graphically, as shown in FIG. 1.

Preparative reverse-phase HPLC can be used to prepare the individual factors in larger quantities. The fractions can be monitored by an agar-well diffusion assay using *Bacillus subtilis* ATCC 6633 as the detecting organism, or by an ultraviolet detector measuring absorption at 254 nm. Another procedure for separating the factors is by chromatography using Sephadex LH-20 as the adsorbent and methanol-water (15:85) as the eluant. Fractions are monitored by bioassay using *Bacillus subtilis* ATCC 6633 as the detecting organism or by reverse-phase high pressure liquid chromatography on silica-gel/$C_{18}$ with 3:1 methanol-water as eluant.

Tunicamycin complex and the individual tunicamycin factors inhibit the growth of certain pathogenic organisms, particularly gram-positive bacteria, fungi, and yeasts, as demonstrated in vitro by standard paper-disc or agar dilution inhibition tests.

In order to illustrate more fully the operation of this invention, using varying fermentation media, the following Examples are provided. However, the scope of the invention is not intended to be limited thereby.

EXAMPLES

Example 1

A medium was prepared for use in the agar slant culture of *Streptomyces chartreusis* Calhoun and Johnson, 1956, NRRL 12338:

| Ingredient | Amount (g/L.) |
| --- | --- |
| Dextrin | 10.0 |
| Yeast extract | 1.0 |
| Enzyme-hydrolyzed casein[1] | 2.0 |
| Beef extract | 1.0 |
| $CoCl_2 \cdot 6H_2O$ | 0.01 |
| Agar | 20.0 |
| Deionized water q.s. to | 1 liter |

[1]N-Z-Amine A (Humko Sheffield Chemical Co., Memphis, Tenn.)

The pH of the medium was adjusted to pH 7.0 before autoclaving.

Spores of *Streptomyces chartreusis* Calhoun and Johnson, 1956, NRRL 12338, were inoculated on a nutrient agar slant made up of the above-identified ingredients, and the thus-inoculated slant was incubated for 7–10 days at a temperature of 30° C. The mature slant culture was then covered with calf serum and scraped with a sterile tool to loosen the spores and mycelia. The suspension was transferred to small tubes and lyophilized for preservation. One lyophilized pellet was used to inoculate each of four 250 ml. flasks, each one containing 50 ml. of sterile vegetative culture medium having the following composition:

| Ingredient | Amount (g/L.) |
| --- | --- |
| Glucose | 15.0 |
| Potato dextrin | 20.0 |
| Soybean grits | 15.0 |
| Corn steep liquor | 10.0 |
| Yeast extract | 1.0 |
| $CaCO_3$ | 2.0 |
| Tap water q.s. to | 1.0 liter |

The inoculated vegetative medium was incubated at 30° C. for 48–72 hours on a shaker rotating through an arc two inches in diameter at 250 RPM. The resulting culture was used either to inoculate small fermentors (the inoculum being approximately 1% per volume of fermentor medium), or to inoculate second stage flasks for the production of a larger volume of mycelia.

An 800 ml. portion of the culture was used to inoculate 103 liters of the following medium in a 165 liter fermentor.

| Ingredient | Amount (g/L.) |
| --- | --- |
| Silicone antifoam agent[1] | 0.2 |
| Glucose | 25.0 |
| Corn starch | 10.0 |
| Meat peptone[2] | 10.0 |
| Enzyme-hydrolyzed casein[3] | 4.0 |
| Blackstrap molasses | 5.0 |
| $MgSO_4 \cdot 7H_2O$ | 0.5 |
| $CaCO_3$ | 2.0 |
| Tap water q.s. to | 103 liters |

[1]Dow-Corning Antifoam A
[2]O.M. Peptone (Amber Laboratories, Juneau, Wisc.)
[3]N-Z-Amine A (Humko Sheffield Chemical Co., Memphis, Tenn.)

This production medium, pH 6.6, was sterilized for about 45 minutes at a temperature of about 121° C. and a pressure of 17 to 19 psi. The sterilized medium, pH 6.5, was inoculated with 0.8% inoculum, aerated with sterile air at the rate of 0.25 v/v/m, stirred with conventional agitators at 200 RPM, and allowed to ferment for about 6 days at a temperature of 30° C.

EXAMPLE 2

Tunicamycin was produced by the fermentation of *Streptomyces chartreusis* Calhoun and Johnson, 1956, NRRL 12338, using a sterile production medium having the following composition:

| Ingredient | Amount (g/L.) |
| --- | --- |
| Silicone antifoam agent[1] | 0.2 |
| Tapioca dextrin | 30.0 |
| Enzyme-hydrolyzed casein[2] | 10.0 |
| Czapek's mineral stock[3] | 2.0 ml/L. |
| Deionized water q.s. to | 100 liters |

[1]Dow Corning Antifoam A
[2]N-Z-Amine A (Humko Sheffield Chemical Co., Memphis, Tenn.)
[3]Czapek's mineral stock is prepared from the following ingredients:

| Ingredient | Amount (g/100 ml) |
| --- | --- |
| KCl | 10.0 |
| $MgSO_4 \cdot 7H_2O$ | 10.0 |
| $FeSO_4 \cdot 7H_2O$ | 0.2 |
| Deionized water q.s. to | 100 ml. |

This production medium had a pH of 6.3, which was adjusted to pH 7.0 using 5 N aqueous potassium hydroxide. The medium was sterilized for about 45 minutes at a temperature of about 121° C. and a pressure of 16 to 18 psi. The post-sterilization pH was 7.0. The sterilized medium was inoculated with 0.8% inoculum and was allowed to ferment for about 5 days at a temperature of 30° C. The fermentation medium was aerated with sterile air at the rate of 0.25 v/v/m, and was stirred with conventional agitators at 250 RPM.

EXAMPLE 3

(a) Recovery and Purification of Tunicamycin

To 85 liters of whole fermentation broth there was added 3% (w/v) of filter aid (Hyflo-Supercel, a diatomaceous earth sold by Johns-Manville Company), and the mixture was filtered through an 18-inch plate filter press. The filter cake in the press was washed with 30 liters of water twice, and the original filtrate and the washes, which contained no or little tunicamycin, were discarded. The filter cake in the press was then extracted successively with 60 liters, 30 liters, and 30 liters of methanol by continuous circulation for 30 minutes each time. The methanolic extracts were combined and concentrated in vacuo to a volume of about 1650 ml. This concentrate was diluted to a volume of 4 liters with water (pH of the solution was 6.6) and allowed to stand for about 16 hours at about 5° C. for complete precipitation to occur. Filter aid (3% w/v, Hyflo-Supercel) was added to the mixture and the tunicamycin precipitate was recovered by filtration. The filter cake was washed with cold water and then extracted four times with 1500 ml. portions of methanol. The extracts were combined, concentrated in vacuo to a volume of about 250 ml., and fifteen volumes of acetone were added to precipitate the tunicamycin complex. The mixture was allowed to stand at 5° C. overnight. The precipitate was recovered by filtration, washed with acetone, and dried, to yield 14.2 g. of crude tunicamycin (ca. 63% pure).

(b) Purification of Crude Tunicamycin

Crude tunicamycin, 40.6 g., was added to 900 ml. of water and the mixture adjusted to pH 10 with ammonium hydroxide in order to effect complete solution. The solution was pumped onto a steel column containing 3.2 liters of silica gel/$C_{18}$ (Whatman LP-1/$C_{18}$, or any commercially available reverse phase silica gel) previously packed in methanol:water (2:1) as described hereinafter in Example 6. Before adding the tunicamycin solution, the column had been washed with 500 ml. of dilute ammonium hydroxide at pH 10. After loading, the column was washed with 800 ml. of dilute ammonium hydroxide at pH 10. The column was then washed with methanol:water (2:1) at a pressure of 450 psi and a flow rate of 100 ml./min. The washing was continued until the impurities were removed, as monitored by analytical HPLC at 25 nm [silica gel/$C_{18}$-methanol:water (3:1)]. The tunicamycin complex was then eluted with methanol:water (4:1). The elution was monitored by analytical HPLC and agar-well diffusion assay using Bacillus subtilis ATCC 6633 as the detecting organism. The fractions containing tunicamycin were combined and concentrated in vacuo to leave a residue. The residue was dissolved in water:dioxane (2:1) and lyophilized. In this manner there was obtained 25.1 g. of pure tunicamycin complex.

(c) Separation of Tunicamycin Factors

Pure tunicamycin complex (300 mg.) was dissolved in water adjusted to pH 10 with ammonium hydroxide. The solution was applied to a steel column containing 140 ml. of silica gel/$C_{18}$. The column was initially packed in methanol:water (2:1), then washed with 50 ml. of dilute ammonium hydroxide (pH 10) prior to loading the tunicamycin solution, and with 100 ml. of dilute ammonium hydroxide (pH 10) immediately after loading. The column was initially developed at 150 psi and a flow rate of 10 ml./min. with methanol:water (2:1), collecting 25 ml. fractions, and the elution was monitored with a UV detector at 254 nm. At fraction 15, the solvent was changed to methanol:water (2.75:1) and at fraction 111 to methanol:water (3:1). The fractions containing single factors were combined, concentrated to a residue, which was dissolved in water:dioxane (2:1) and lyophilized. The yields of each factor were as follows:

| Factor | Fractions | Weight (mg) |
| --- | --- | --- |
| $A_1$ | 30–33 | 4.3 |
| $A_2$ | 35–39 | 13.2 |
| $B_1$ | 43–52 | 39.4 |
| $B_2$ | 54–58 | 8.3 |
| $C_1$ | 67–84 | 66.8 |
| $C_2$ | 91–101 | 37.0 |
| $D_1 + D_2$ | 115–121 | 18.2 |

EXAMPLE 4

Large Scale Isolation of Tunicamycin

Fermentation broth, 4550 liters, was adjusted to pH 6.5 using concentrated aqueous hydrochloric acid, and filtered through a filter press employing 1% Celite 545 (diatomaceous earth, Johns-Manville Corp.) filter aid. The filter cake was washed with water until the effluent was clear and the filtrate and water wash were discarded. The filter cake was blown dry and removed from the press. This dried filter cake was slurried with 1000 liters of methanol and the slurry held overnight at a temperature of about 5° C. The slurry was filtered through a filter press and the methanolic filtrate reserved. The filter cake was then extracted with 2×400 liters of methanol. These extracts were combined with the previously reserved methanolic filtrate and concentrated in vacuo to a volume of about 180 liters. This solution was adjusted to pH 6.3 with concentrated aqueous hydrochloric acid and allowed to stand at 5° C. overnight in order for complete precipitation to occur. Diatomaceous earth (Celite 545, Johns-Manville Corp.), 4.5 kg., was added to the solution containing the precipitate, and the mixture was filtered. The filter cake was washed twice with 10 liter portions of water, then slurried in 60 liters of methanol, with stirring for about 15 minutes at a temperature of about 20° C., and filtered. This extraction of the filter cake with 60 liter portions of methanol was repeated three more times. All of the methanol extracts were combined and concentrated in vacuo to a volume of about 10 liters. To this concentrate, 150 liters of acetone was added, with stirring, to precipitate the tunicamycin. The mixture was chilled overnight at a temperature of about 5° C., and filtered using a 24-inch Büchner funnel. The solid on the filter was washed with two equal volumes of acetone, and dried in a vacuum oven to yield 680 gm. of semi-purified tunicamycin.

EXAMPLE 5

Purification of Tunicamycin Complex

A solution was prepared from 40 gm. of tunicamycin complex (from the above preparation) and 800 ml. of water, adjusted to pH 10 using concentrated aqueous ammonium hydroxide. The solution was applied to a Chromatospac Prep HPLC (Jobin Yvon, Division d'Instruments S.A., Longjumean, France) column containing 4 liters of silica gel/$C_{18}$ (reverse-phase resin) equilibrated in methanol:water (2:1). The column was developed with 10 liters of methanol:water (2:1) to remove impurities. The effluent was monitored at 280 nm with a recording spectrophotometer.

The tunicamycin complex was then eluted from the column with 35 liters of methanol:water (5:1) at a flow rate of about 60 ml./min., and a pressure of about 90 psi, collecting fractions each measuring 500 ml. in volume. Fractions containing the tunicamycin factors were combined and concentrated to a volume of about 200-300 ml. Dioxane, 200 ml., was added, and the solution lyophilized. A white powder weighing 27 gm., identified as pure tunicamycin complex, was obtained.

EXAMPLE 6

Preparation of Silica Gel/$C_{18}$ Reverse Phase Resin for HPLC

Step 1: Hydrolysis

LP-1 silica gel (1000 g. from Quantum Corp., now Whatman) is added to a mixture of 1650 ml. of concentrated sulfuric acid and 1650 ml. of concentrated nitric acid in a 5 l. round bottom flask and shaken for proper suspension. The mixture is heated on a steam bath overnight (16 hours) with a water-jacketed condenser attached to the flask.

The mixture is cooled in an ice bath and carefully filtered using a sintered glass funnel. The silica gel is washed with deionized water until the pH is neutral. The silica gel is then washed with acetone (4 l.) and dried under vacuum at 100° C. for 2 days.

Step 2: First Silylation

The dry silica gel from Step 1 is transferred to a round bottom flask and suspended in toluene (3.5 l.). The flask is heated on a steam bath for 2 hours to azeotrope off some residual water. Octadecyltrichlorosilane (321 ml, Aldrich Chemical Company) is added and the reaction mixture refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 l.) and acetone (3 l.), and then air-dried overnight (16-20 hours). The dried silica gel is suspended in 3.5 l. of acetonitrile:water (1:1) in a 5 l. flask, stirred carefully at room temperature for 2 hours, filtered, washed with acetone (3 l.) and air-dried overnight.

Step 3: Second Silylation

The procedure from the first silylation is repeated using 200 ml. of octadecyltrichlorosilane. The suspension is refluxed at 60° C. for 2 hours while stirring carefully. The final product is recovered by filtration, washed with toluene (3 l.), methanol (6 l.), and then dried under vacuum at 50° C. overnight (16-20 hours).

An additional step to fully methylate any free hydroxyl groups (capping) remaining on the silica gel can be carried out, if desired. Both types of silica gel/$C_{18}$ (the product of Step 3, supra, or the product of the following Step 4) have been successfully used for tunicamycin purification and factor separation.

Step 4: Methylation

The octadecyl silica gel from Step 3 is added to 3.3 l. of toluene in a 12-liter, 3-neck flask equipped with a stirrer, a thermometer, a Dean-Stark trap, a reflux condenser, and a heating mantle. The mixture is stirred and refluxed until no more water is collected in the Dean-Stark trap. The mixture is then cooled to about 65° C. and 200 ml. of bis(trimethylsilyl)acetamide is added dropwise. The mixture is stirred and refluxed for about 2.5 hours, cooled to room temperature, and filtered. The filter cake is washed successively with 4-liter portions of toluene, methanol, and acetone, and dried under vacuum on the filter funnel. The silica gel/$C_{18}$ then is air dried overnight to yield about 900 g. of product, having 20-22% carbon by elemental analysis.

What is claimed is:

1. A method for preparing tunicamycin which comprises cultivating *Streptomyces chartreusis* Calhoun and Johnson, 1956, NRRL 12338 in a culture medium containing assimilable sources of carbon, nitrogen, and inorganic salts under submerged aerobic conditions until a substantial amount of tunicamycin is produced.

2. The method of claim 1 wherein the tunicamycin is recovered from the culture medium.

3. A method for preparing tunicamycin $A_1$ which comprises preparing tunicamycin according to the method defined in claim 2; and separating tunicamycin $A_1$ from other co-produced tunicamycin factors.

4. A method for preparing tunicamycin $A_2$ which comprises preparing tunicamycin according to the method defined in claim 2; and separating tunicamycin $A_2$ from other co-produced tunicamycin factors.

5. A method for preparing tunicamycin $B_1$ which comprises preparing tunicamycin according to the method defined in claim 2; and separating tunicamycin $B_1$ from other co-produced tunicamycin factors.

6. A method for preparing tunicamycin $B_2$ which comprises preparing tunicamycin according to the method defined in claim 2; and separating tunicamycin $B_2$ from other co-produced tunicamycin factors.

7. A method for preparing tunicamycin $C_1$ which comprises preparing tunicamycin according to the method defined in claim 2; and separating tunicamycin $C_1$ from other co-produced tunicamycin factors.

8. A method for preparing tunicamycin $C_2$ which comprises preparing tunicamycin according to the method defined in claim 2; and separating tunicamycin $C_2$ from other co-produced tunicamycin factors.

9. A method for preparing tunicamycin $D_1$ which comprises preparing tunicamycin according to the method defined in claim 2; and separating tunicamycin $D_1$ from other co-produced tunicamycin factors.

10. A method for preparing tunicamycin $D_2$ which comprises preparing tunicamycin according to the method defined in claim 2; and separating tunicamycin $D_2$ from other co-produced tunicamycin factors.

11. A biologically pure culture of the strain of *Streptomyces chartreusis* Calhoun and Johnson, 1956, NRRL 12338, and all natural and artificial variants and mutants thereof, which on culturing in a medium containing assimilable sources of carbon, nitrogen, and inorganic salts under submerged aerobic conditions produces tunicamycin.

* * * * *